(12) United States Patent
Lou et al.

(10) Patent No.: US 10,064,596 B2
(45) Date of Patent: Sep. 4, 2018

(54) CONTROLLING X-RAY DOSE OF CT SCAN

(71) Applicant: Shenyang Neusoft Medical Systems Co., Ltd., Shenyang (CN)

(72) Inventors: Shanshan Lou, Shenyang (CN); Gang Fang, Shenyang (CN); Jiangwei Zhao, Shenyang (CN)

(73) Assignee: Shenyang Neusoft Medical Systems Co., Ltd., Shenyang (CN)

( * ) Notice: Subject to any disclaimer, the term of this patent is extended or adjusted under 35 U.S.C. 154(b) by 35 days.

(21) Appl. No.: 14/863,467

(22) Filed: Sep. 24, 2015

(65) Prior Publication Data

US 2016/0089101 A1    Mar. 31, 2016

(30) Foreign Application Priority Data

Sep. 30, 2014  (CN) .......................... 2014 1 0526058

(51) Int. Cl.
*A61B 6/03*  (2006.01)
*A61B 6/00*  (2006.01)

(52) U.S. Cl.
CPC .............. *A61B 6/545* (2013.01); *A61B 6/032* (2013.01); *A61B 6/40* (2013.01); *A61B 6/405* (2013.01); *A61B 6/4085* (2013.01); *A61B 6/48* (2013.01); *A61B 6/488* (2013.01); *A61B 6/52* (2013.01); *A61B 6/5205* (2013.01); *A61B 6/5211* (2013.01); *A61B 6/54* (2013.01); *A61B 6/542* (2013.01)

(58) Field of Classification Search
CPC ........... A61B 6/032; A61B 6/40; A61B 6/405; A61B 6/4085; A61B 6/48; A61B 6/488; A61B 6/52; A61B 6/5205; A61B 6/5211; A61B 6/54; A61B 6/542; A61B 6/545
USPC ........................ 378/4, 16, 62, 98.7, 108–110
See application file for complete search history.

(56) References Cited

U.S. PATENT DOCUMENTS

| 5,450,462 | A | * | 9/1995 | Toth ........................ A61B 6/032 |
| | | | | 378/108 |
| 5,485,494 | A | * | 1/1996 | Williams ............... A61B 6/032 |
| | | | | 378/110 |

(Continued)

FOREIGN PATENT DOCUMENTS

| CN | 1535100 A | 10/2004 |
| CN | 101115442 A | 1/2008 |

(Continued)

*Primary Examiner* — Allen C. Ho
(74) *Attorney, Agent, or Firm* — Kilpatrick Townsend & Stockton, LLP

(57) ABSTRACT

A method for controlling an X-ray dose of a CT scan includes: setting an initial X-ray dose; performing a first CT scan with the initial X-ray dose to obtain an initial scan image; setting a region of interest (ROI) in the initial scan image; calculating a subsequent X-Ray dose with image values of the ROI in the initial scan image; perform an additional CT scan with the calculated subsequent X-Ray dose to obtain an average image; before receiving an end instruction, repeating the following operations: recalculating a subsequent X-Ray dose with image values of the ROI in the average image and performing an additional CT scan with the calculated subsequent X-Ray dose to obtain a new average image; and saving the average image when receiving the end instruction.

18 Claims, 4 Drawing Sheets

(56) References Cited

U.S. PATENT DOCUMENTS

| | | | |
|---|---|---|---|
| 5,625,662 A * | 4/1997 | Toth | H05G 1/26 378/108 |
| 5,822,393 A * | 10/1998 | Popescu | A61B 6/032 378/108 |
| 5,867,555 A * | 2/1999 | Popescu | A61B 6/032 378/16 |
| 6,385,280 B1 * | 5/2002 | Bittl | A61B 6/032 378/106 |
| 6,404,844 B1 * | 6/2002 | Horiuchi | A61B 6/032 378/16 |
| 6,459,765 B1 * | 10/2002 | Ganin | A61B 6/00 378/108 |
| 6,490,337 B1 * | 12/2002 | Nagaoka | A61B 6/032 378/16 |
| 6,501,819 B2 * | 12/2002 | Unger | A61B 6/405 378/207 |
| 6,507,639 B1 * | 1/2003 | Popescu | A61B 6/032 378/108 |
| 6,754,301 B2 * | 6/2004 | Horiuchi | A61B 6/032 378/16 |
| 6,904,127 B2 * | 6/2005 | Toth | A61B 6/032 378/108 |
| 6,987,828 B2 * | 1/2006 | Horiuchi | G01N 23/046 378/108 |
| 7,042,977 B2 * | 5/2006 | Dafni | A61B 6/032 378/16 |
| 7,054,406 B2 * | 5/2006 | Ikeda | A61B 6/032 378/4 |
| 7,082,183 B2 * | 7/2006 | Toth | A61B 6/032 378/16 |
| 7,103,139 B2 * | 9/2006 | Nagaoka | A61B 6/032 378/16 |
| 7,106,824 B2 * | 9/2006 | Kazama | A61B 6/032 378/110 |
| 7,113,569 B2 * | 9/2006 | Okumura | A61B 6/032 378/150 |
| 7,142,630 B2 * | 11/2006 | Suzuki | A61B 6/542 378/108 |
| 7,145,982 B2 * | 12/2006 | Ikeda | A61B 6/032 378/16 |
| 7,215,733 B2 * | 5/2007 | Nabatame | A61B 6/032 378/110 |
| 7,274,770 B2 * | 9/2007 | Nederpelt | G06T 5/40 378/97 |
| 7,280,635 B2 * | 10/2007 | Toth | A61B 6/032 378/108 |
| 7,336,762 B2 * | 2/2008 | Seto | A61B 6/032 378/110 |
| 7,460,635 B2 * | 12/2008 | Fujimoto | A61B 6/032 378/16 |
| 7,587,023 B2 * | 9/2009 | Hur | A61B 6/481 378/110 |
| 7,602,880 B2 * | 10/2009 | Hirokawa | A61B 6/032 378/108 |
| 7,636,416 B2 * | 12/2009 | Miyazaki | A61B 6/032 378/108 |
| 7,668,286 B2 * | 2/2010 | Tsuyuki | A61B 6/032 378/16 |
| 7,756,243 B2 * | 7/2010 | Gohno | A61B 6/032 378/16 |
| 7,813,471 B2 * | 10/2010 | Hirokawa | A61B 6/032 378/4 |
| 7,945,013 B2 * | 5/2011 | Goto | A61B 5/4869 378/16 |
| 7,983,457 B2 * | 7/2011 | Toth | A61B 6/032 378/16 |
| 8,031,831 B2 * | 10/2011 | Zou | A61B 6/032 378/108 |
| 8,126,109 B2 * | 2/2012 | Tsukagoshi | A61B 6/032 378/51 |
| 8,155,263 B2 * | 4/2012 | Wu | A61B 6/032 378/16 |
| 8,175,217 B2 * | 5/2012 | Sugaya | A61B 6/032 378/16 |
| 8,265,227 B2 * | 9/2012 | Boudry | H05G 1/46 378/110 |
| 8,649,479 B2 * | 2/2014 | De Man | A61B 6/032 378/16 |
| 8,699,658 B2 * | 4/2014 | Yu | A61B 6/032 378/16 |
| 8,699,661 B2 * | 4/2014 | Jang | A61B 6/4007 378/37 |
| 8,744,039 B2 * | 6/2014 | Hirokawa | A61B 6/032 378/108 |
| 8,744,040 B2 * | 6/2014 | Sugaya | A61B 6/032 378/16 |
| 8,798,228 B2 * | 8/2014 | Chandrashekarappa | A61B 6/032 378/16 |
| 8,845,190 B2 * | 9/2014 | Foos | A61B 6/4405 378/207 |
| 8,848,860 B2 * | 9/2014 | Yazaki | A61B 6/488 378/16 |
| 9,014,461 B2 * | 4/2015 | Hayashida | G06T 7/0012 378/132 |
| 9,020,220 B2 * | 4/2015 | Nukui | A61B 6/488 382/128 |
| 9,119,560 B2 * | 9/2015 | Kohara | A61B 6/032 |
| 9,269,128 B2 * | 2/2016 | Kim | G06T 5/002 |
| 9,380,984 B2 * | 7/2016 | Li | A61B 6/032 |
| 9,478,049 B2 * | 10/2016 | Bippus | G06T 11/006 |
| 9,558,570 B2 * | 1/2017 | Liang | |
| 9,592,022 B2 * | 3/2017 | Larson | A61B 6/032 |
| 9,636,074 B2 * | 5/2017 | Lou | A61B 6/5264 |
| 9,836,825 B2 * | 12/2017 | Lou | G06T 5/002 |
| 9,877,695 B2 * | 1/2018 | Lou | A61B 6/544 |
| 9,911,208 B2 * | 3/2018 | Zhou | G06T 11/008 |
| 2002/0085672 A1 | 7/2002 | Ganin | |
| 2007/0140428 A1 | 6/2007 | Toth | |
| 2011/0091008 A1 | 4/2011 | Hirokawa et al. | |
| 2011/0150187 A1 | 6/2011 | Boudry et al. | |
| 2012/0057672 A1 | 3/2012 | Jang et al. | |
| 2012/0087474 A1 | 4/2012 | Foos et al. | |
| 2012/0114093 A1 | 5/2012 | Yu et al. | |

FOREIGN PATENT DOCUMENTS

| | | |
|---|---|---|
| CN | 101506904 A | 8/2009 |
| CN | 102436006 A | 5/2012 |
| CN | 102697514 A | 10/2012 |
| CN | 102949194 A | 3/2013 |
| CN | 103907132 A | 7/2014 |

* cited by examiner

FIG. 1(Abstract Figure)

CONTROLLING X-RAY DOSE OF CT SCAN

BACKGROUND

The present invention is directed to computed tomography (CT).

NEUSOFT MEDICAL SYSTEMS CO., LTD. (NMS), founded in 1998 with its world headquarters in China, is a leading supplier of medical equipment, medical IT solutions, and healthcare services. NMS supplies medical equipment with a wide portfolio, including CT, MRI, digital X-ray machine, Ultrasound, PET (Positron Emission Tomography), Linear Accelerator, and Biochemistry Analyser. Currently, NMS' products are exported to over 60 countries and regions around the globe, serving more than 5,000 renowned customers. NMS's latest successful developments, such as 128 Multi-Slice CT Scanner System, Superconducting MRI, Linear Accelerator, and PET products, have led China to become a global high-end medical equipment producer. As an integrated supplier with extensive experiences in large medical equipment, NMS has been committed to the study of avoiding secondary potential harm caused by excessive X-ray irradiation to the subject during the CT scan process.

As described below, conventional CT scanners have their inadequacies and limitations. It is desirable to have improved methods and systems for performing CT scanning.

BRIEF DESCRIPTION OF DRAWINGS

Features of the present disclosure are illustrated by way of example and not limited in the following figure(s), in which like numerals indicate like elements, in which.

DETAILED DESCRIPTION

The present invention is directed to computed tomography (CT).

Computed Tomography (CT) refers to scanning a certain region of a subject (e.g., a patient) with a certain dose of X-ray beam to obtain a scan image for diagnosis by a doctor. The so-called dose refers to a total amount of radiation energy measured voltage, current and time for scanning with an X-ray beam. Typically, under a certain voltage, the magnitude of X-ray dose may be characterized by an integration of current with time in milliampere-seconds.

In conventional technology, the X-ray dose for scanning is generally set according to experiences or some relevant parameters. Further, to ensure that the resultant scan image is sufficiently clear to satisfy diagnosis requirements, the X-ray dose for scanning is typically set to be excessively large. Unfortunately, an excessively large X-ray dose may pose a radiation hazard for the subject. For a CT scanner system, an excessively large X-ray dose may also cause more load for the bulb tube and thereby reduce the service life of the bulb tube. Thus is to be appreciated that embodiments of the present invention provide methods and systems for calibrating and reducing X-ray dose in CT scanning.

For simplicity and illustrative purposes, the present disclosure is described by referring mainly to an example thereof. In the following description, numerous specific details are set forth in order to provide a thorough understanding of the present disclosure. It will be readily apparent however, that the present disclosure may be practiced without limitation to these specific details. In other instances, some methods and structures have not been described in detail so as not to unnecessarily obscure the present disclosure. As used herein, the terms "a" and "an" are intended to denote at least one of a particular element, the term "includes" means includes but not limited to, the term "including" means including but not limited to, and the term "based on" means based at least in part on.

In the present disclosure, a plurality of CT scan are performed with low X-ray doses, and a CT scan process is stopped and a resultant scan image is saved when the scan image obtained after a certain CT scan is completed is sufficient for diagnosis. According to the multi-scan scheme of the present disclosure, the total used X-ray dose may be approached the minimum dose but the resultant scan image can be guaranteed as suitable for diagnosis.

Figure 1:
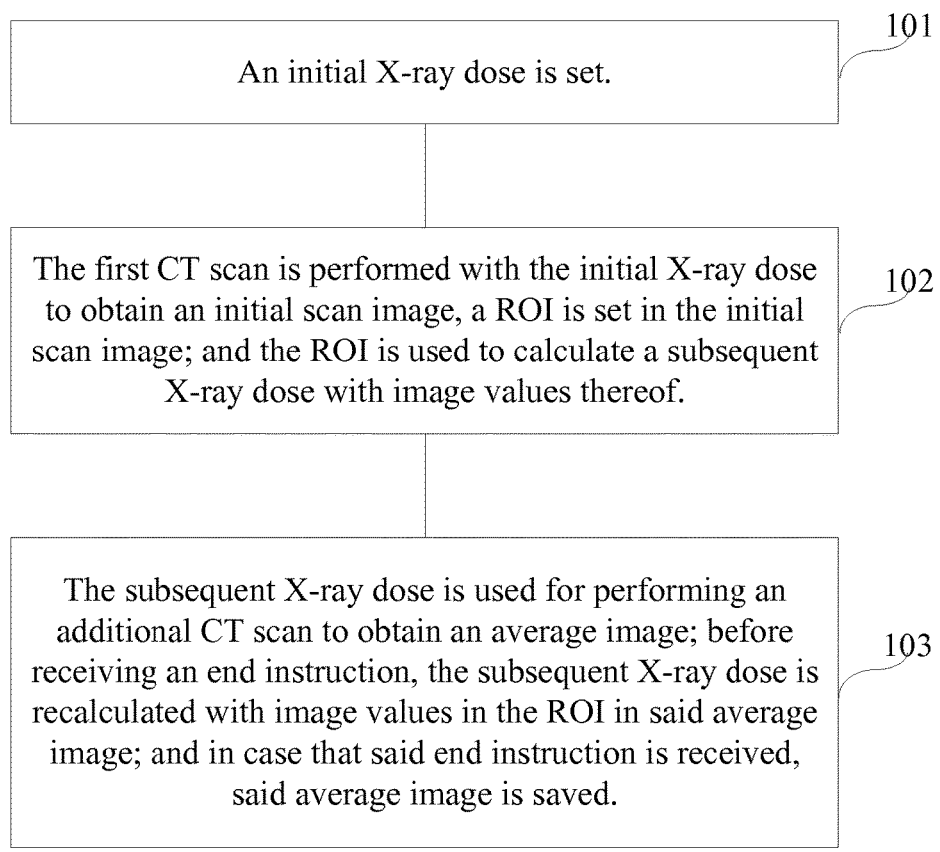
FIG. 1 is a schematic flowchart of a method for controlling an X-ray dose for a CT scan according to an example of the present disclosure.

As shown in FIG. 1, in an example, the method according to the present disclosure may be as follows. Depending on the implementation, one or more steps may be added, removed, modified, replaced, repeated, rearranged, and/or overlapped, and should not limit the scope of claims.

At block 101, an initial X-ray dose is set.

This block is the preparation operation of the method. Prior to the CT scan, a scanning protocol may be selected in advance. The so called scanning protocol is a combination of parameters such as current, voltage, etc. used for the CT scan. Different region of a subject have different tissue structure features, and therefore there are generally different scanning protocols corresponding to different regions of a subject to be scanned. The conventional technology of CT scans may be referred to for the selection of scanning protocol.

The final scan image is formed using information from multiple CT scans. The first CT scan can be different from subsequent CT scan in terms of X-ray dose control. The X-ray dose used for the first CT scan is the initial X-ray dose and is typically set beforehand. For example, the initial X-ray dose may be set as 10% of a fixed reference X-ray dose according to the scanning protocol.

At block 102, the first CT scan is performed with the initial X-ray dose to obtain an initial scan image, and a ROI is set in the initial scan image. The ROI is used to calculate a subsequent X-Ray dose with image values thereof.

After completing the setting of the initial X-ray dose, the first CT scan is performed with the initial X-ray dose to obtain an initial scan image. However, the initial scan image obtained from the first scan may be not sufficient for diagnosis. Therefore, a region of interest (ROI) may be selected in the initial scan image by the operator according to practical conditions of the scanned subject. For example, ROI generally refers to a region that is likely to exhibit lesion characteristics in the scan image or a region that may be observed in subsequent diagnosis. Then, some necessary parameters may be obtained with image values in the ROI so as to calculate the subsequent X-Ray dose value required for the subsequent CT scan.

Figure 2:
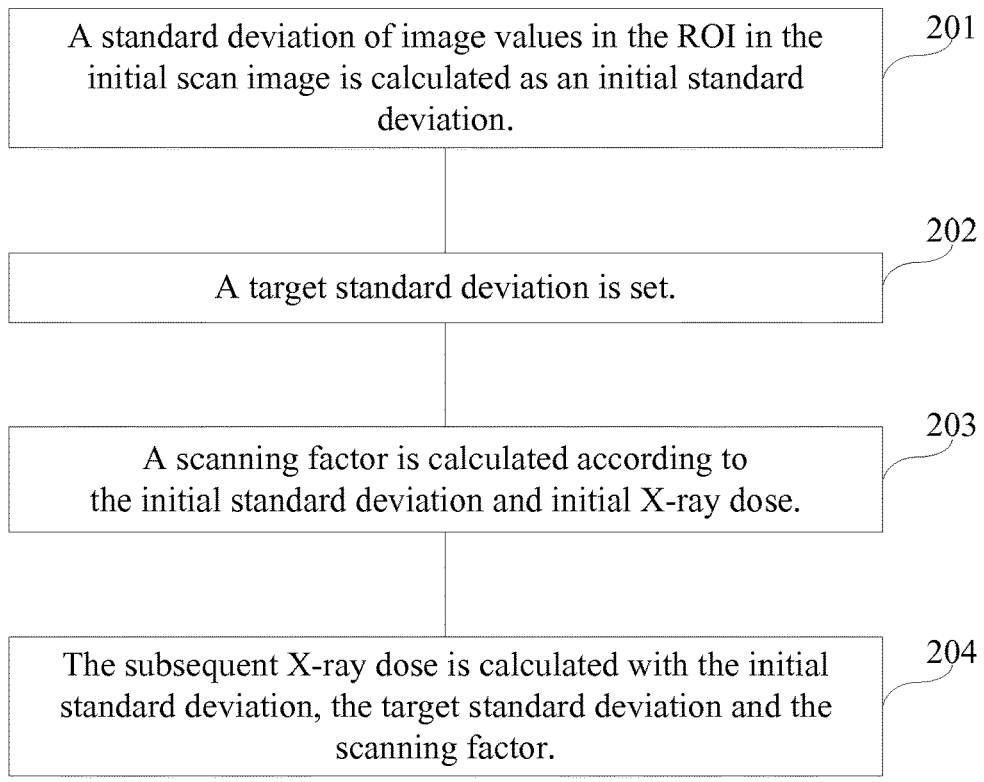
FIG. 2 is a schematic flowchart of a method for calculating subsequent X-Ray dose with image values in a region of interest (ROI) in the initial scan image according to an example of the present disclosure.

Specifically, the process of calculating the subsequent X-Ray dose with image values in the ROI in the initial scan image is shown in FIG. 2, which may include the following blocks. Depending on the implementation, one or more steps may be added, removed, modified, replaced, repeated, rearranged, and/or overlapped, and should not limit the scope of claims.

At block 201, after obtaining the initial scan image by the first CT scan with the initial X-ray dose R, a standard deviation σ of image values in the ROI in the initial scan image is calculated as an initial standard deviation $\sigma_{ori}$.

The initial standard deviation $\sigma_{ori}$ is the standard deviation σ of image values in the ROI after the first CT scan, which is calculated according to Formula (01):

$$\sigma_{ori} = \sigma = \sqrt{\frac{1}{N}\sum_{i=1}^{N}(x_i - \bar{x})^2} \ ; \qquad \text{Formula (01)}$$

wherein, the $\sigma_{ori}$ is the initial standard deviation; the σ is the standard deviation of image values in the ROI; the N is a number of pixels in the ROI; the $x_i$ is an image value of the $i^{th}$ pixel; and the $\bar{x}$ is an average image value of pixels in the ROI.

At block 202, a target standard deviation $\sigma_{obj}$ is set.

In an example, the target standard deviation $\sigma_{obj}$ may be set according to the initial standard deviation $\sigma_{ori}$. For example, it may be set as 1/K of the initial standard deviation $\sigma_{ori}$, wherein the K is an integer greater than or equal to 2.

At block 203, a scanning factor D is calculated according to the initial standard deviation $\sigma_{ori}$ and initial X-ray dose R.

In general, the initial standard deviation $\sigma_{ori}$ and the initial X-ray dose R are often in a proportional relationship. The coefficient for maintaining the proportional relationship between them is referred to as a scanning factor. The specific value of the scanning factor depends on the subject under scanning. For example, parameters such as the absorption conversion constant, the penetration characteristic coefficient, the scanning layer thickness, and/or the pixel size data of the scanned object may influence the scanning factor. Once set, the scanning factor generally remains constant in the scanning process.

The relationship among the scanning factor, the initial standard deviation $\sigma_{ori}$ and the initial X-ray dose R is described in Formula (02):

$$\sigma_{ori}^2 = D/R \qquad \text{Formula (02)}.$$

Here, both the initial standard deviation $\sigma_{ori}$ and the initial X-ray dose R are known, it is possible to derive the scanning factor D.

At block 204, the subsequent X-Ray dose R' is calculated with the initial standard deviation $\sigma_{ori}$, the target standard deviation $\sigma_{obj}$ and the scanning factor D, wherein, the calculation Formula (03) for calculating the subsequent X-Ray dose R' with the initial standard deviation $\sigma_{ori}$, the scanning factor D and the standard deviation σ is:

$$R' = \begin{cases} \dfrac{D}{4\sigma_{obj}^2 - \sigma_{ori}^2}, & 4\sigma_{obj}^2 - \sigma_{ori}^2 > 0 \\[2mm] \dfrac{D}{\sigma_{ori}^2}, & 4\sigma_{obj}^2 - \sigma_{ori}^2 \leq 0 \end{cases} ; \qquad \text{Formula (03)}$$

wherein, the R' is the subsequent X-Ray dose,
the D is the scanning factor,
the $\sigma_{obj}$ is the target standard deviation, and
the $\sigma_{ori}$ is the initial standard deviation.

At block 103, the subsequent X-Ray dose R' is used for performing an additional CT scan to obtain an average image. Before receiving an end instruction, a subsequent X-Ray dose R' is recalculated with image values in the ROI in the average image; and in case that the end instruction is received, the average image is saved.

After the block 102, block 103 may be performed to calculate a subsequent X-Ray dose R' for the second CT scan. It should be understood that before receiving the end instruction, block 103 may be executed for multiple times. After each CT scan is completed, a new subsequent X-Ray dose R' and a new average image are obtained for the next execution of block 103. For simple description, the X-ray doses used for each subsequent CT scans (including the second CT scan) will be referred to as a subsequent X-Ray dose R' collectively below; and the scan image obtained by a corresponding calculation process after each CT scan with a subsequent X-Ray dose R' is referred to as an average image collectively. That is to say, there may be a plurality of the subsequent X-Ray doses R' and the average images in the whole CT scan process for a region of a subject according to the present disclosure.

Figure 3:
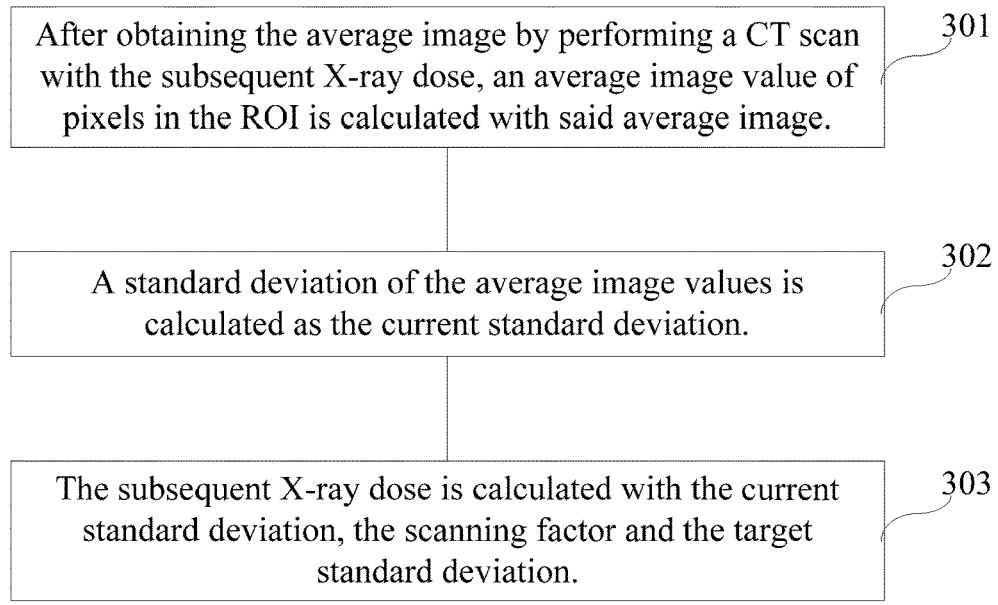
FIG. 3 is a schematic flowchart of a method for calculating subsequent X-Ray dose with image values in a ROI in the average image according to an example of the present disclosure.

Specifically, referring to FIG. 3, the performing a CT scan with a subsequent X-Ray dose R' to obtain an average image and recalculating the subsequent X-Ray dose R' with image values in the ROI of the average image in block 103 may include the following blocks.

At block 301, after obtaining the average image by performing a CT scan with the subsequent X-Ray dose R', an average image value of pixels in the ROI is calculated with the average image.

In this block, after completing the second or subsequent CT scan with the subsequent X-Ray dose R', an additional scan image may be obtained directly by this CT scan, and then a cumulative average of the additional scan and the average image obtained previously may be calculated so as to obtain a new average image and a new average image value of pixels in the ROI of the new average image, specifically according to formula (04):

$$x_{mean} = \tfrac{1}{2}(x_{mean}' + x) \qquad \text{Formula (04)};$$

where, the $x_{mean}$ is the average image value of each pixels in the ROI after current CT scan, namely image value of each pixels in the ROI of the new average image; the $x_{mean}'$ is the average image value of each pixels in the ROI after the previous CT scan, namely image value of each pixels in the ROI of the average image obtained previously; the x is a reconstructed image value of each pixels in the ROI obtained by current CT scan, namely image value of each pixels in the ROI of the additional scan image obtained directly by current CT scan.

It is to be understood that when the previous CT scan is the first CT scan, then $x'_{mean} = x_1$, the $x_1$ is the image value of each pixels in the ROI after the first CT scan, namely the image value of each pixels in the ROI of the initial scan image.

At block 302, a standard deviation σ of the average image values is calculated as the current standard deviation $\sigma_{cur}$.

In each subsequent CT scan (including the second CT scan), a standard deviation σ calculated with the average image values is referred to as a current standard deviation $\sigma_{cur}$ collectively, that is, there may be a plurality of current standard deviations $\sigma_{cur}$ according to the present disclosure. Calculation of the current standard deviations $\sigma_{cur}$ may be based on formula (05):

$$\sigma_{cur} = \sqrt{\frac{1}{N} \sum_{i=1}^{N} (y_i - \overline{y})^2} \; ; \qquad \text{Formula (05)}$$

where the $\sigma_{cur}$ is the current standard deviation; the N is the number of pixels in the ROI; the $y_i$ is the average value of the $i^{th}$ pixel after current CT scan; and the $\overline{y}$ is the average value of the average image values of pixels in the ROI after current CT scan.

It can be seen that formula (05) is similar to formula (01), because they adopt the same principle for calculating standard deviation σ.

At block 303, the subsequent X-Ray dose R' is calculated with the current standard deviation $\sigma_{cur}$, the scanning factor D and the target standard deviation $\sigma_{obj}$.

The scanning factor and the target standard deviation have been obtained as described above. The current standard deviation $\sigma_{cur}$ has also been derived in block 302. Then it is possible to calculate the subsequent X-Ray dose for next CT scan according to formula (06):

$$R_{next} = \begin{cases} \dfrac{D}{4\sigma_{obj}^2 - \sigma_{cur}^2}, & 4\sigma_{obj}^2 - \sigma_{cur}^2 > 0 \\ \dfrac{D}{\sigma_{cur}^2}, & 4\sigma_{obj}^2 - \sigma_{cur}^2 \leq 0 \end{cases} \qquad \text{Formula (06)}$$

wherein, the $R_{next}$ is the subsequent X-Ray dose, the D is the scanning factor, the $\sigma_{obj}$ is the target standard deviation, and the $\sigma_{cur}$ is the current standard deviation. It should be understood that the current standard deviation as described in the present disclosure is essentially a parameter reflecting image noise. Whereas multiple CT scan are performed with an expectation of reducing the image noise. Therefore, in order to guarantee that the noise level of obtained average image will decrease successively after each CT scan, the value range of the $R_{next}$ may be as following formula:

$$\tfrac{1}{3} R_{mean} < R_{next} < R_{mean};$$

wherein the $R_{mean}$ is the equivalent X-ray dose corresponding to the average image value obtained by previous CT scans.

It should also be understood that after multiple CT scans, the current standard deviation and the initially set target standard deviation may approach each other too closely, that is, when the difference between them is smaller than a predetermined threshold, it may be impossible to calculate a subsequent X-Ray dose $R_{next}$ effectively. If the end instruction is not received yet, that is, the operator wants to perform more subsequent CT scans to guarantee resultant average image suitable for diagnosis, the target standard deviation may have to be reset. In an example, the target standard deviation may be reset as 1/K of the current standard deviation, wherein the K is an integer greater than or equal to 2.

Since the resultant average images will become clearer and clearer in the process of multiple CT scan, when the operator consider that the resultant average image is clear enough for diagnosis after a certain CT scan is completed, he or she may send the end instruction. Upon receiving the end instruction, the next CT scan will not be performed no longer, and the average image obtained by the last CT scan will be saved.

After a plurality of CT scan according to the method shown in the present disclosure, it is possible to stop the scanning process just when the scan image exhibits a sufficient definition, thereby avoiding the occurrence of over large X-ray dose. In fact, according to the method of the present disclosure, the sum of X-ray doses used in each of the multiple CT scan is smaller than the X-ray dose preset based on a corresponding scanning protocol.

Figure 4:
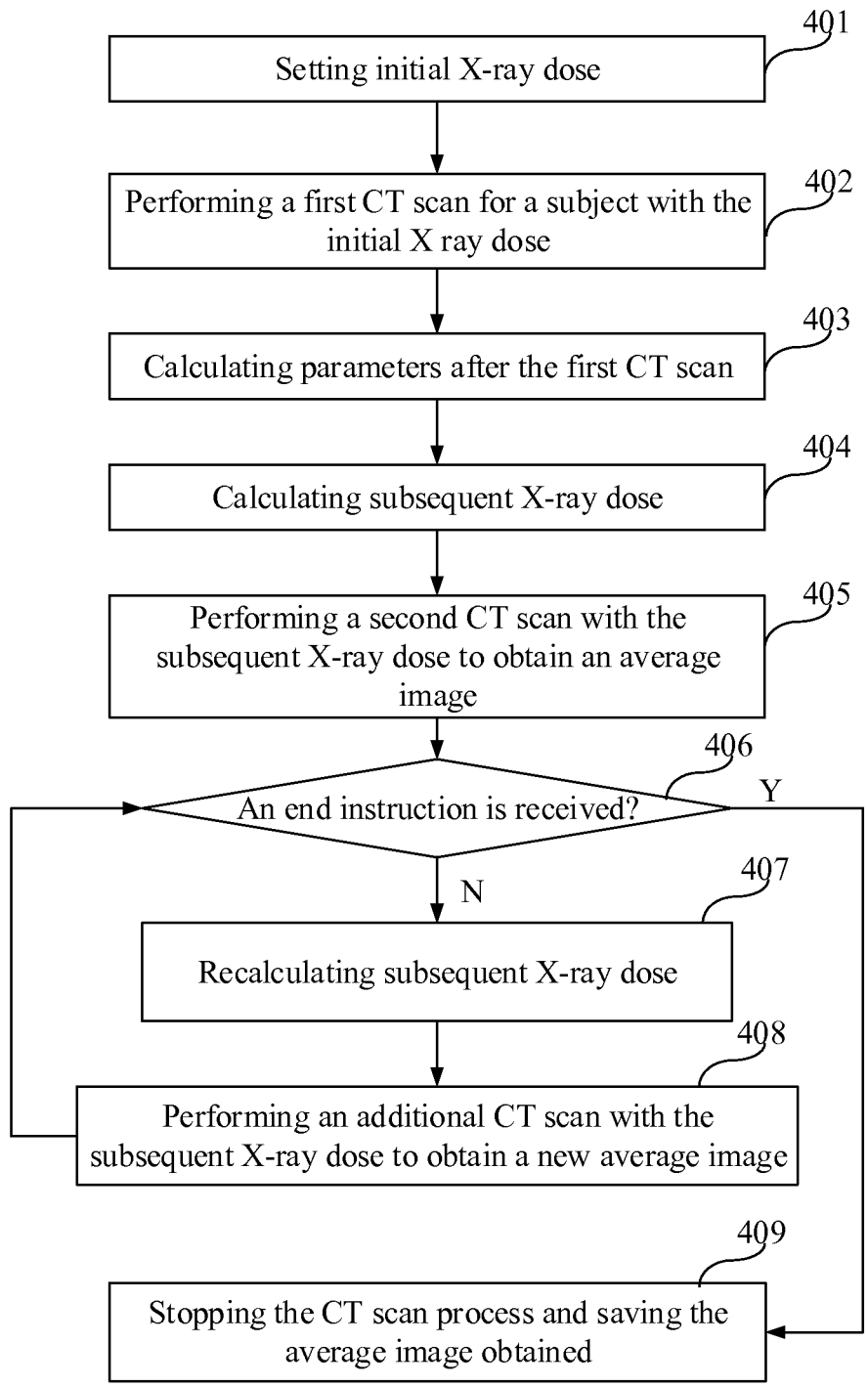
FIG. 4 is a schematic flowchart of a method for controlling an X-ray dose for a CT scan according to another example of the present disclosure.

Referring to FIG. 4, which is a flow diagram illustrating a method for controlling an X-ray dose for a CT scan according to an example of the present disclosure. Depending on the implementation, one or more steps may be added, removed, modified, replaced, repeated, rearranged, and/or overlapped, and should not limit the scope of claims. As shown in FIG. 4, the method generally includes: block 401 for setting an initial X ray dose; block 402 for performing a first CT scan for a subject with the initial X ray dose; block 403 for calculating parameters such as a scanning factor and a target standard deviation after the first CT scan; block 404 for calculating subsequent X-Ray dose R'; block 405 for performing a second CT scan with the subsequent X-Ray dose R' to obtain an average image; block 406 for determining whether an end instruction is received or not; block 407 for, before receiving the end instruction (the determination result is NO in block 406), recalculating a subsequent X-Ray dose; and block 408 for performing an additional CT scan with the subsequent X-Ray dose to obtain a new average image; while block 409 for, in case of receiving the end instruction (the determination result is YES in block 406), stopping the CT scan process and saving the average image obtained after the last CT scan.

As can be known from the above disclosure, by performing multiple CT scans and stopping the CT scan process upon a resultant scan image exhibiting a sufficient definition, a sufficiently clear scan image may be obtained with a minimum X-ray dose but not an over large X-ray dose. In this way, it may not only reduce influence on the scanned subject, but also reduce the work load of CT bulb tube and hence extending the service life of instruments.

Figure 5:
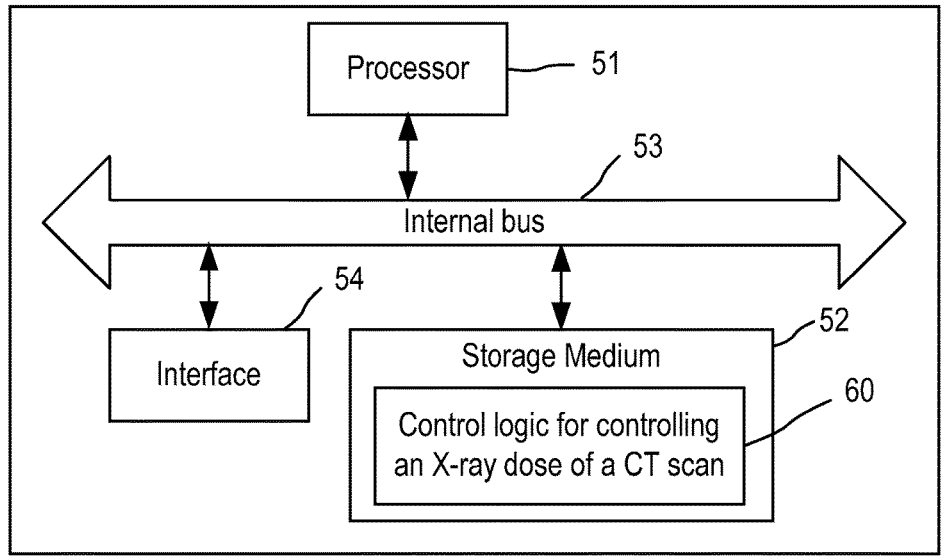
FIG. 5 is a schematic diagram of hardware structure of a device for controlling an X-ray dose for a CT scan according to an example of the present disclosure.
Figure 6:
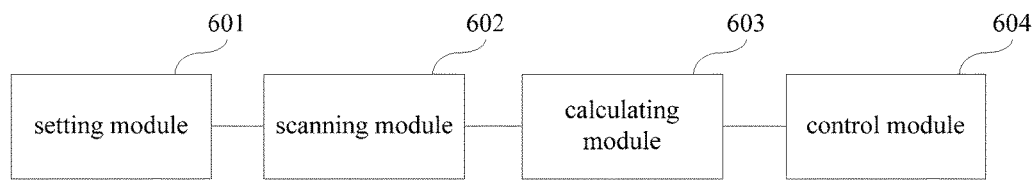
FIG. 6 is a schematic diagram of functional modules of a control logic for controlling an X-ray dose for a CT scan corresponding to the method shown in FIG. 1.

Referring to FIG. 5, corresponding to the above-mentioned method, the present disclosure also provides an apparatus for controlling an X-ray dose for a CT scan. As shown in FIG. 5, the apparatus includes a processor 51 such as a CPU and a machine readable storage medium 52, wherein the processor 51 and the machine readable storage medium 52 are generally interconnected via an internal bus 53. In other possible implementations, the apparatus may further include an external interface 54 to be able to communicate with other equipment or components.

In different examples, the machine readable storage medium 52 may be RAM (Random Access Memory), volatile memory, non-volatile memory, flash memory, memory drive (such as hard disk drive), solid state hard disk, any type of memory disc (such as optical disk, DVD etc.) or similar storage medium or combination thereof.

Further, the machine readable storage medium 52 has a control logic 60 for controlling an X-ray dose of a CT scan stored thereon. Functionally, the control logic includes:

a setting module 601 for setting an initial X-ray dose and a ROI in a scan image;

a scanning module 602 for performing a first CT scan with the initial X-ray dose R to obtain an initial scan image or performing an additional scan with a subsequent X-Ray dose R' to obtain an average image;

a calculating module 603 for calculating a subsequent X-Ray dose R' with image values of the ROI in the initial scan image or recalculating a subsequent X-Ray dose with image R' values of the ROI in the average image;

wherein the calculating module 603 repeats the calculations of subsequent X-Ray doses R'; and the scanning module 602 repeats the CT scan with the subsequent X-Ray doses R';

a control module 604 for sending an end instruction and saving the average image. Before receiving the end instruction, the calculating module 603 repeats the calculations of subsequent X-Ray doses R', and the scanning module 602 repeats the CT scan with subsequent X-Ray doses R'.

Herein below, a software implementation will be describe as an example to further explain how the apparatus for controlling an X-ray dose of a CT scan execute the control logic 60. In this example, the disclosed control logic 60 may be understood as computer instructions stored in the machine readable storage medium 52. When the processor 51 on the apparatus of the present disclosure invokes instructions corresponding to the control logic 60 stored on the machine readable storage medium 52, the processor is caused to:

set an initial X-ray dose R;

perform a first CT scan with the initial X-ray dose R to obtain an initial scan image;

set a ROI in the initial scan image;

calculate a subsequent X-Ray dose R' with image values of the ROI in the initial scan image;

perform an additional CT scan with the calculated subsequent X-Ray dose R' to obtain an average image;

repeat the following operations before receiving an end instruction: recalculating a new subsequent X-Ray dose $R_{next}$ with image values of the ROI in the average image and performing an additional CT scan with the new subsequent X-Ray dose $R_{next}$ to obtain a new average image; and save the new average image when receiving the end instruction.

Furthermore, the machine readable instructions further cause the processor 51 to:

calculate a standard deviation σ of image values of the ROI in the initial scan image as the initial standard deviation $\sigma_{ori}$;

set a target standard deviation $\sigma_{obj}$;

calculate a scanning factor D according to the initial standard deviation $\sigma_{ori}$ and the initial X-ray dose R; and calculate the subsequent X-Ray dose R' with the initial standard deviation $\sigma_{ori}$, the target standard deviation $\sigma_{obj}$ and the scanning factor D, Wherein, the scanning factor D is calculated according to the initial standard deviation $\sigma_{ori}$ and the initial X-ray dose R with the following formula:

$$\sigma_{ori}^2 = D/R;$$

where, the $\sigma_{ori}$ is the initial standard deviation,
the D is the scanning factor,
the R is the initial X-ray dose.

The subsequent X-Ray dose R' is calculated according to the initial standard deviation $\sigma_{ori}$, the target standard deviation $\sigma_{obj}$ and the scanning factor D with the following formula:

$$R' = \begin{cases} \dfrac{D}{4\sigma_{obj}^2 - \sigma_{ori}^2}, & 4\sigma_{obj}^2 - \sigma_{ori}^2 > 0 \\ \dfrac{D}{\sigma_{ori}^2}, & 4\sigma_{obj}^2 - \sigma_{ori}^2 \leq 0 \end{cases};$$

where, the R' is the subsequent X-Ray dose,
the D is the scanning factor,
the $\sigma_{obj}$ is the target standard deviation, and
the $\sigma_{ori}$ is the initial standard deviation.

The target standard deviation $\sigma_{obj}$ may be set as 1/K of the initial standard deviation $\sigma_{ori}$, wherein the K is an integer greater than or equal to 2.

Furthermore, the machine readable instructions further cause the processor 51 to:

calculate a standard deviation σ of image values of the ROI in the average image as the current standard deviation $\sigma_{cur}$; and calculate the new subsequent X-Ray dose $R_{next}$ with the current standard deviation $\sigma_{cur}$, the scanning factor D and the target standard deviation $\sigma_{obj}$.

Wherein, the new subsequent X-Ray dose $R_{next}$ is calculated according to the current standard deviation $\sigma_{cur}$, the scanning factor D and the target standard deviation $\sigma_{obj}$ with the following formula:

$$R_{next} = \begin{cases} \dfrac{D}{4\sigma_{obj}^2 - \sigma_{cur}^2}, & 4\sigma_{obj}^2 - \sigma_{cur}^2 > 0 \\ \dfrac{D}{\sigma_{cur}^2}, & 4\sigma_{obj}^2 - \sigma_{cur}^2 \leq 0 \end{cases};$$

wherein, the $R_{next}$ is the new subsequent X-Ray dose,
the D is the scanning factor,
the $\sigma_{obj}$ is the target standard deviation, and
the $\sigma_{cur}$ is the current standard deviation.

Furthermore, when a difference obtained by subtracting the current standard deviation $\sigma_{cur}$ from the target standard deviation $\sigma_{obj}$ is less than a preset threshold and the end instruction is not received yet, the machine readable instructions further cause the processor 51 to: reset the target standard deviation $\sigma_{obj}$ as 1/K of the current standard deviation $\sigma_{cur}$, wherein the K is an integer greater than or equal to 2; and then recalculate the new subsequent X-Ray dose $R_{next}$ with the current standard deviation $\sigma_{cur}$, the scanning factor D and the reset target standard deviation $\sigma_{obj}$.

Furthermore, the machine readable instructions further cause the processor 51 to:

perform a CT scan with the calculated subsequent X-Ray dose R' to obtain additional scan image data; and calculate a cumulative average of the additional scan image data with the image data of the initial scan image or the average image data obtained previously according to the following formula to obtain average image data, $$x_{mean} = \begin{cases} \dfrac{1}{2}(x_{ori} + x), & \text{for first additional } CT \text{ scan} \\ \dfrac{1}{2}(x'_{mean} + x), & \text{for } n^{th} \text{ additional } CT \text{ scan}, n \geq 2 \end{cases};$$

wherein, the $x_{mean}$ is the value of the average image data,
the $x_{ori}$ is the value of the image data of the initial scan image, the $x_{mean}'$ is the value of the average image data obtained previously, and the x is the value of the additional scan image data; and reconstruct the average image based on the average image data.

The above are only preferred examples of the present disclosure is not intended to limit the disclosure within the spirit and principles of the present disclosure, any changes made, equivalent replacement, or improvement in the protection of the present disclosure should contain within the range.

The methods, processes and units described herein may be implemented by hardware (including hardware logic circuitry), software or firmware or a combination thereof. The term 'processor' is to be interpreted broadly to include a processing unit, ASIC, logic unit, or programmable gate array etc. The processes, methods and functional units may all be performed by the one or more processors; reference in this disclosure or the claims to a 'processor' should thus be interpreted to mean 'one or more processors'.

Further, the processes, methods and functional units described in this disclosure may be implemented in the form of a computer software product. The computer software product is stored in a storage medium and comprises a plurality of instructions for making a processor to implement the methods recited in the examples of the present disclosure.

The figures are only illustrations of an example, wherein the units or procedure shown in the figures are not necessarily essential for implementing the present disclosure. Those skilled in the art will understand that the units in the device in the example can be arranged in the device in the examples as described, or can be alternatively located in one or more devices different from that in the examples. The units in the examples described can be combined into one module or further divided into a plurality of sub-units.

Although the flowcharts described show a specific order of execution, the order of execution may differ from that which is depicted. For example, the order of execution of two or more blocks may be changed relative to the order shown. Also, two or more blocks shown in succession may be executed concurrently or with partial concurrence. All such variations are within the scope of the present disclosure.

Throughout the present disclosure, the word "comprise", or variations such as "comprises" or "comprising", will be understood to imply the inclusion of a stated element, integer or step, or group of elements, integers or steps, but not the exclusion of any other element, integer or step, or group of elements, integers or steps.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

The invention claimed is:

1. A method for controlling an X-ray dose of a CT scan, the method comprises:
setting an initial X-ray dose;
performing a first CT scan with the initial X-ray dose to obtain an initial scan image;
setting a region of interest (ROI) in the initial scan image;
calculating a subsequent X-Ray dose with image values of the ROI in the initial scan image;
performing an additional CT scan with the calculated subsequent X-Ray dose to obtain an average image;
repeating the following operations before receiving an end instruction: recalculating a new subsequent X-Ray dose with image values of the ROI in the average image and performing an additional CT scan with the new subsequent X-Ray dose to obtain a new average image; and
saving the new average image when receiving the end instruction;
wherein the image values of the ROI comprise a parameter reflecting image noise of the ROI in the initial scan image or the average image;
wherein calculating the subsequent X-Ray dose with image values of the ROI in the initial scan image comprises:
calculating a standard deviation of image values of the ROI in the initial scan image as an initial standard deviation;
setting a target standard deviation;
calculating a scanning factor according to the initial standard deviation and the initial X-ray dose; and
calculating the subsequent X-Ray dose with the initial standard deviation, the target standard deviation, and the scanning factor.

2. The method according to claim 1, wherein a formula for calculating the standard deviation of image values of the ROI in the initial scan image as the initial standard deviation is:

$$\sigma_{ori} = \sigma = \sqrt{\frac{1}{N}\sum_{i=1}^{N}(x_i - \bar{x})^2};$$

wherein, the $\sigma_{ori}$ is the initial standard deviation;
the $\sigma$ is the standard deviation of image values of the ROI in the initial scan image;
the N is a number of pixels in the ROI in the initial scan image;
the $x_i$ is an image value of the $i^{th}$ pixel in the ROI in the initial scan image; and
the $\bar{x}$ is an average image value of pixels in the ROI in the initial scan image.

3. The method according to claim 1, wherein a formula for calculating the scanning factor according to the initial standard deviation and the initial X-ray dose is:

$$\sigma_{ori}^2 = D/R_{ori};$$

where, the $\sigma_{ori}$ is the initial standard deviation,
the D is the scanning factor, and
the $R_{ori}$ is the initial X-ray dose.

4. The method according to claim 1, wherein a formula for calculating the subsequent X-Ray dose with the initial standard deviation, the standard deviation, and the scanning factor is:

$$R' = \begin{cases} \dfrac{D}{4\sigma_{obj}^2 - \sigma_{ori}^2}, & 4\sigma_{obj}^2 - \sigma_{ori}^2 > 0 \\ \dfrac{D}{\sigma_{ori}^2}, & 4\sigma_{obj}^2 - \sigma_{ori}^2 \leq 0 \end{cases};$$

where, the R' is the subsequent X-Ray dose,
the D is the scanning factor,
the $\sigma_{obj}$ is the target standard deviation, and
the $\sigma_{ori}$ is the initial standard deviation.

5. The method according to claim 1, wherein setting the target standard deviation comprises:
   setting the target standard deviation as 1/K of the initial standard deviation, wherein the K is an integer greater than or equal to 2.

6. The method according to claim 1, wherein recalculating the new subsequent X-Ray dose with image values of the ROI in the average image comprises:
   calculating a standard deviation of image values of the ROI in the average image as a current standard deviation; and
   calculating the new subsequent X-Ray dose with the current standard deviation, the scanning factor, and the target standard deviation.

7. The method according to claim 6, wherein a formula for calculating the new subsequent X-Ray dose with the current standard deviation, the scanning factor, and the target standard deviation is:

$$R_{next} = \begin{cases} \dfrac{D}{4\sigma_{obj}^2 - \sigma_{cur}^2}, & 4\sigma_{obj}^2 - \sigma_{cur}^2 > 0 \\ \dfrac{D}{\sigma_{cur}^2}, & 4\sigma_{obj}^2 - \sigma_{cur}^2 \leq 0 \end{cases};$$

where, the $R_{next}$ is the new subsequent X-Rays dose,
the D is the scanning factor,
the $\sigma_{obj}$ is the target standard deviation, and
the $\sigma_{cur}$ is the current standard deviation.

8. The method according to claim 6, wherein a formula for calculating the standard deviation of image values of the ROI in the average image as the current standard deviation is:

$$\sigma_{cur} = \sqrt{\dfrac{1}{n}\sum_{i=1}^{N}(y_i - \bar{y})^2};$$

where the $\sigma_{cur}$ is the current standard deviation;
the N is a number of pixels in the ROI in the average image;
the $y_i$ is an image value of the $i^{th}$ pixel in the ROI in the average image; and
the $\bar{y}$ is an average image value of pixels in the ROI in the average image.

9. The method according to claim 6, wherein calculating the new subsequent X-Ray dose with the current standard deviation, the scanning factor, and the target standard deviation further comprises:
   when a difference obtained by subtracting the current standard deviation from the target standard deviation is less than a preset threshold and the end instruction is not received yet, resetting the target standard deviation as 1/K of the current standard deviation, wherein the K is an integer greater than or equal to 2; and then
   recalculating the new subsequent X-Ray dose with the current standard deviation, the scanning factor, and the reset target standard deviation.

10. The method according to claim 1, wherein performing the additional CT scan with the calculated subsequent X-Ray dose to obtain the average image or the new average image comprises:
    performing a CT scan with the calculated subsequent X-Ray dose to obtain additional scan image data;
    calculating a cumulative average of the additional scan image data with the image data of the initial scan image or the average image data obtained previously according to the following formula to obtain average image data, $$x_{mean} = \begin{cases} \dfrac{1}{2}(x_{ori} + x), & \text{for first additional } CT \text{ scan} \\ \dfrac{1}{2}(x'_{mean} + x), & \text{for } n^{th} \text{ additional } CT \text{ scan}, n \geq 2 \end{cases},$$

wherein, the $x_{mean}$ is value of the average image data, the $x_{ori}$ is value of image data of the initial scan image, the $x_{mean}'$ is value of the average image data obtained previously, and the x is value of the additional scan image data; and
    reconstructing the average image based on the average image data.

11. An apparatus for controlling an X-ray dose of a CT scan, comprising:
    a processor which invokes machine readable instructions corresponding to a control logic for controlling an X-ray dose of a CT scan stored in a storage medium so as to:
    set an initial X-ray dose;
    perform a first CT scan with the initial X-ray dose to obtain an initial scan image;
    set a region of interest (ROI) in the initial scan image;
    calculate a subsequent X-Ray dose with image values of the ROI in the initial scan image;
    perform an additional CT scan with the calculated subsequent X-Ray dose to obtain an average image;
    repeat the following operations before receiving an end instruction: recalculating a new subsequent X-Ray dose with image values of the ROI in the average image and performing an additional CT scan with the new subsequent X-Ray dose to obtain a new average image; and
    save the new average image when receiving the end instruction,
    wherein the image values of the ROI comprise a parameter reflecting image noise of the ROI in the initial scan image or the average image;
    wherein, for calculating the subsequent X-Ray dose with image values of the ROI in the initial scan image, the machine readable instructions further cause the processor to:
    calculate a standard deviation of image values of the ROI in the initial scan image as an initial standard deviation;
    set a target standard deviation;
    calculate a scanning factor according to the initial standard deviation and the initial X-ray dose; and
    calculate the subsequent X-Ray dose with the initial standard deviation, the target standard deviation, and the scanning factor.

12. The apparatus according to claim 11, wherein a formula for the processor to calculate the scanning factor according to the initial standard deviation and the initial X-ray dose is:

$$\sigma_{ori}^2 = D/R_{ori};$$

where, the $\sigma_{ori}$ is the initial standard deviation,
the D is the scanning factor, and
the $R_{ori}$ is the initial X-ray dose.

13. The apparatus according to claim 11, wherein a formula for the processor to calculate the subsequent X-Ray dose with the initial standard deviation, the target standard deviation, and the scanning factor is:

$$R' = \begin{cases} \dfrac{D}{4\sigma_{obj}^2 - \sigma_{ori}^2}, & 4\sigma_{obj}^2 - \sigma_{ori}^2 > 0 \\ \dfrac{D}{\sigma_{ori}^2}, & 4\sigma_{obj}^2 - \sigma_{ori}^2 \leq 0 \end{cases};$$

where, the R' is the subsequent X-Ray dose,
the D is the scanning factor,
the $\sigma_{obj}$ is the target standard deviation, and
the $\sigma_{ori}$ is the initial standard deviation.

14. The apparatus according to claim 11, wherein the machine readable instructions further cause the processor to:
set the target standard deviation as 1/K of the initial standard deviation, wherein the K is an integer greater than or equal to 2.

15. The apparatus according to claim 11, wherein the machine readable instructions further cause the processor to:
calculate a standard deviation of image values of the ROI in the average image as a current standard deviation; and
calculate the new subsequent X-Ray dose with the current standard deviation, the scanning factor, and the target standard deviation.

16. The apparatus according to claim 15, wherein a formula for the processor to calculate the new subsequent X-Ray dose with the current standard deviation, the scanning factor, and the target standard deviation is:

$$R_{next} = \begin{cases} \dfrac{D}{4\sigma_{obj}^2 - \sigma_{cur}^2}, & 4\sigma_{obj}^2 - \sigma_{cur}^2 > 0 \\ \dfrac{D}{\sigma_{cur}^2}, & 4\sigma_{obj}^2 - \sigma_{cur}^2 \leq 0 \end{cases};$$

where, the $R_{next}$ is the new subsequent X-Ray dose,
the D is the scanning factor,
the $\sigma_{obj}$ is the target standard deviation, and
the $\sigma_{cur}$ is the current standard deviation.

17. The apparatus according to claim 16, wherein the machine readable instructions further cause the processor to:
reset the target standard deviation as 1/K of the current standard deviation when a difference obtained by subtracting the current standard deviation from the target standard deviation is less than a preset threshold and the end instruction is not received yet, wherein the K is an integer greater than or equal to 2; and then
recalculate the new subsequent X-Ray dose with the current standard deviation, the scanning factor, and the reset target standard deviation.

18. The apparatus according to claim 11, wherein the machine readable instructions further cause the processor to:
perform a CT scan with the calculated subsequent X-Ray dose to obtain additional scan image data;
calculate a cumulative average of the additional scan image data with the image data of the initial scan image or the average image data obtained previously according to the following formula to obtain average image data, $$x_{mean} = \begin{cases} \dfrac{1}{2}(x_{ori} + x), & \text{for first additional } CT \text{ scan} \\ \dfrac{1}{2}(x'_{mean} + x), & \text{for } n^{th} \text{ additional } CT \text{ scan}, n \geq 2 \end{cases};$$

wherein, the $x_{mean}$ is value of the average image data, the $x_{ori}$ is value of image data of the initial scan image, the $x_{mean}'$ is value of the average image data obtained previously, and the x is value of the additional scan image data; and
reconstruct the average image based on the average image data.

* * * * *